US012805803B2

(12) United States Patent
Peters, Jr. et al.

(10) Patent No.: US 12,805,803 B2
(45) Date of Patent: Nov. 24, 2026

(54) IN-CANAL EAR TIPS

(71) Applicant: Bose Corporation, Framingham, MA (US)

(72) Inventors: Thomas J. Peters, Jr., Sudbury, MA (US); Liam Robert Kelly, Dorchester, MA (US); Yang Liu, Sudbury, MA (US); Andrew D. Dominijanni, Newton, MA (US); Christian Trott, Charleston, SC (US); Christopher Borradaile, Framingham, MA (US); Shawn J. Prevoir, Northborough, MA (US)

(73) Assignee: Bose Corporation, Framingham, MA (US)

( * ) Notice: Subject to any disclaimer, the term of this patent is extended or adjusted under 35 U.S.C. 154(b) by 1156 days.

(21) Appl. No.: 17/639,180

(22) PCT Filed: Aug. 28, 2020

(86) PCT No.: PCT/US2020/048361
§ 371 (c)(1),
(2) Date: Feb. 28, 2022

(87) PCT Pub. No.: WO2021/041778
PCT Pub. Date: Mar. 4, 2021

(65) Prior Publication Data

US 2022/0323009 A1 Oct. 13, 2022

Related U.S. Application Data

(60) Provisional application No. 62/894,040, filed on Aug. 30, 2019.

(51) Int. Cl.
*A61B 5/291* (2021.01)
*A61B 5/00* (2006.01)
(Continued)

(52) U.S. Cl.
CPC ............ *A61B 5/6817* (2013.01); *A61B 5/291* (2021.01); *A61B 5/386* (2021.01); *H04R 1/1016* (2013.01);
(Continued)

(58) Field of Classification Search
CPC .. H04R 2460/11; H04R 1/1016; H04R 1/105; H04R 25/60; H04R 25/656;
(Continued)

(56) References Cited

U.S. PATENT DOCUMENTS 4,781,196 A * 11/1988 Killion .................. A61B 5/389 600/379
2002/0027996 A1 * 3/2002 Leedom ................ H04R 25/65 381/328
(Continued)

FOREIGN PATENT DOCUMENTS

WO WO-2018103861 A1 * 6/2018 ........... A61B 5/6817

*Primary Examiner* — Eun Hwa Kim

(57) ABSTRACT

An ear tip for an earpiece including a body, an insertion end, and a retention structure. Some examples include an elongated fin along a portion of an outer leg of the retention structure. Some examples include an extended insertion end configured to insert further into a user's ear canal and including a mushroom cap for providing contact with an interior portion of the user's ear canal and to form an acoustic seal. Some examples may include an umbrella associated with the insertion end, between the mushroom cap and the body. Electrically conductive elements may be associated with any of the elongated fin, the umbrella, and the mushroom cap, to provide electrical contact with the user's skin for sensing electrical signals or for delivery of electrical stimulation.

15 Claims, 3 Drawing Sheets

(51) Int. Cl.
*A61B 5/386* (2021.01)
*H04R 1/10* (2006.01)
*A61B 5/251* (2021.01)
*A61B 5/263* (2021.01)
*H04R 25/00* (2006.01)

(52) U.S. Cl.
CPC .............. *H04R 1/105* (2013.01); *A61B 5/251* (2021.01); *A61B 5/263* (2021.01); *A61B 2560/0468* (2013.01); *A61B 2560/06* (2013.01); *A61B 2562/0209* (2013.01); *A61B 2562/164* (2013.01); *H04R 25/60* (2013.01); *H04R 25/656* (2013.01); *H04R 2225/77* (2013.01); *H04R 2460/11* (2013.01)

(58) Field of Classification Search
CPC .. H04R 2225/77; H04R 1/016; H04R 1/1091; A61B 5/6817; A61B 5/291; A61B 5/386; A61B 5/251; A61B 5/263; A61B 2560/0468; A61B 2560/06; A61B 2562/0209; A61B 2562/164; A61B 5/6815; A61B 5/6816
See application file for complete search history.

(56) References Cited

U.S. PATENT DOCUMENTS

| | | | | |
|---|---|---|---|---|
| 2018/0235540 | A1* | 8/2018 | Kirszenblat .......... | A61B 5/6803 |
| 2019/0200112 | A1* | 6/2019 | Briggs ................ | H04R 1/1016 |

* cited by examiner

IN-CANAL EAR TIPS

BACKGROUND

This disclosure generally relates to configurations for ear tips for use with earpieces.

SUMMARY

Aspects and examples are directed to ear tips having components that allow enhanced retention or enhanced insertion into an ear canal, or both, each of which may provide surface contact locations to accommodate one or more electrodes. The electrodes enable capturing of bioelectrical signals and/or providing stimulation of nerves through application of electricity.

According to one aspect, an ear tip for an earpiece is provided that includes a body, an insertion end coupled to the body and configured to be at least partially inserted into a human ear canal, a mushroom cap coupled to a distal end of the insertion end and configured to form an acoustic seal in the ear canal, and one or more electrically conductive elements associated with the mushroom cap and configured to provide electrical contact in the ear canal, between an entrance to the ear canal and a first bend in the ear canal.

Some examples also include a retention structure including an outer leg configured to conform, at least in part, to a cymba concha portion of the ear. Further examples may also include one or more electrically conductive contacts associated with the retention structure and configured to provide electrical contact with the cymba concha. In some examples, the electrically conductive contacts are disposed on an elongated fin running at least a portion of the length of the outer leg.

Certain examples also include an umbrella associated with the insertion end, disposed between the body and the mushroom cap and configured to make contact near an entrance to the ear canal. Various examples may include one or more electrically conductive contacts associated with the umbrella to provide one or more electrodes in contact with the ear near an entrance to the ear canal.

Some examples include an umbrella divided into multiple discontinuous segments. Certain examples the umbrella is bifurcated into two opposing segments.

According to another aspect, an ear tip for an earpiece is provided that includes a body, an insertion end coupled to the body and configured to be at least partially inserted into a human ear canal, a retention structure coupled to the body and including an outer leg configured to conform, at least in part, to a cymba concha portion of the ear, and an elongated fin running at least a portion of the length of the outer leg and configured to provide additional contact area with the cymba concha than the outer leg alone.

Various examples include an electrically conductive contact disposed on the elongated fin to provide an electrode in contact with the cymba concha.

Certain examples include an umbrella associated with the insertion end and configured to form an acoustic seal near an entrance to the ear canal. The umbrella may have one or more electrically conductive contacts associated with the umbrella to provide one or more electrodes in contact with the ear near an entrance to the ear canal.

Some examples include a mushroom cap coupled to a distal end of the insertion end, the mushroom cap having one or more electrically conductive elements configured to provide electrical contact in the ear canal between an entrance to the ear canal and a first bend in the ear canal. Such examples may further include an umbrella associated with the insertion end, disposed between the body and the mushroom cap and configured to make contact with the ear near an entrance to the ear canal.

Still other aspects, examples, and advantages of these exemplary aspects and examples are discussed in detail below. Examples disclosed herein may be combined with other examples in any manner consistent with at least one of the principles disclosed herein, and references to "an example," "some examples," "an alternate example," "various examples," "one example" or the like are not necessarily mutually exclusive and are intended to indicate that a particular feature, structure, or characteristic described may be included in at least one example. The appearances of such terms herein are not necessarily all referring to the same example.

BRIEF DESCRIPTION OF THE DRAWINGS

Various aspects of at least one example are discussed below with reference to the accompanying figures, which are not intended to be drawn to scale. The figures are included to provide illustration and a further understanding of the various aspects and examples, and are incorporated in and constitute a part of this specification, but are not intended as a definition of the limits of the invention. In the figures, identical or nearly identical components illustrated in various figures may be represented by a like numeral. For purposes of clarity, not every component may be labeled in every figure. In the figures.

DETAILED DESCRIPTION

This disclosure is directed to configurations of an ear tip with enhanced retention, enhanced insertion into an ear canal, and accommodation for mechanical and electrical contact with a wearer's skin to detect bioelectrical signals, for example, electroencephalogram (EEG) signals, and other health parameters, and/or to deliver an electrical signal to the ear, for example, for nerve stimulation. Typical EEG devices are comprised of a series of electrodes attached to a skull cap. However, these devices are uncomfortable, bulky, inconvenient, and not suitable for daily-life situations. The present disclosure relates to an ear tip capable of measuring bioelectrical signals such as EEG signals from the brain and/or providing nerve stimulation. The ear tip includes a body, which may be configured to accommodate an earbud including an acoustic transducer, a positioning and retaining structure, and an end configured to be partially inserted into a wearer or user's ear canal and which may include a hollow passage to provide acoustic coupling from the acoustic transducer to the ear canal of the user. The ear tip may further include one or more electrically conductive elements arranged on an outer surface of various of the above described structures.

Figure 1:
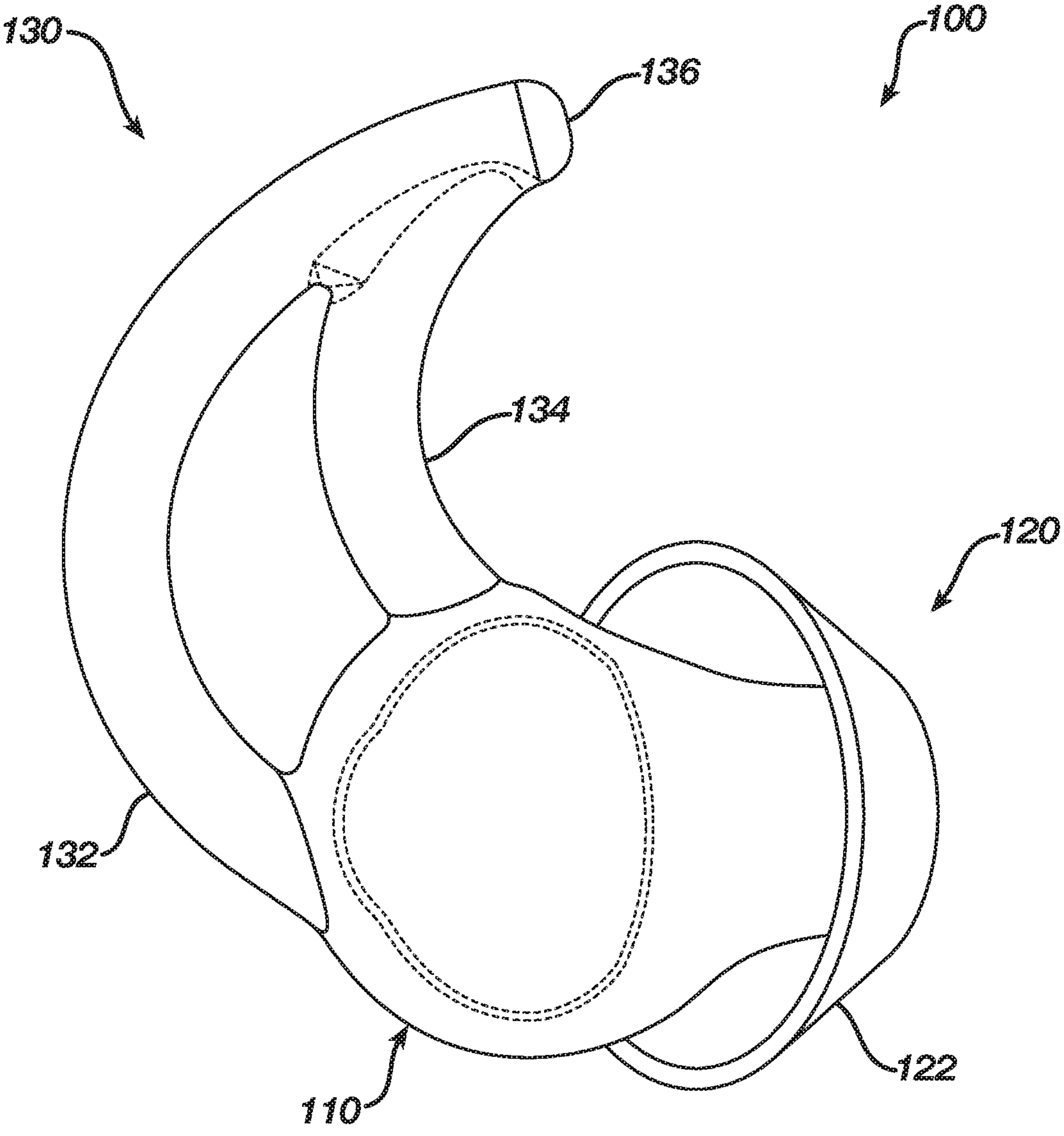
FIG. 1 is an example ear tip.

FIG. 1 illustrates an example ear tip 100 including a body 110, an insertion end 120, and a retaining structure 130. The body 110 may include a cavity to accommodate an earbud that may include various electronics and one or more acoustic transducers for the production of sound into the ear canal and/or for the detection of sound within the ear canal (e.g., a feedback microphone) or exterior to the ear canal (e.g., a feedforward microphone), and/or may include electronics for providing and/or processing electrical signals to or from electrically and/or ionically conductive elements formed in combination with either of the insertion end 120 or the retaining structure 130, or both. The insertion end 120 is configured to fit at least partially into a person's ear canal and includes an umbrella 122 to at least partially form an acoustic seal against the user's skin. The retaining structure 130 is configured to position and hold the ear tip 100 in place when worn, and may include an outer leg 132 and, optionally, an inner leg 134, each of which meet at a tip 136.

Figure 2:
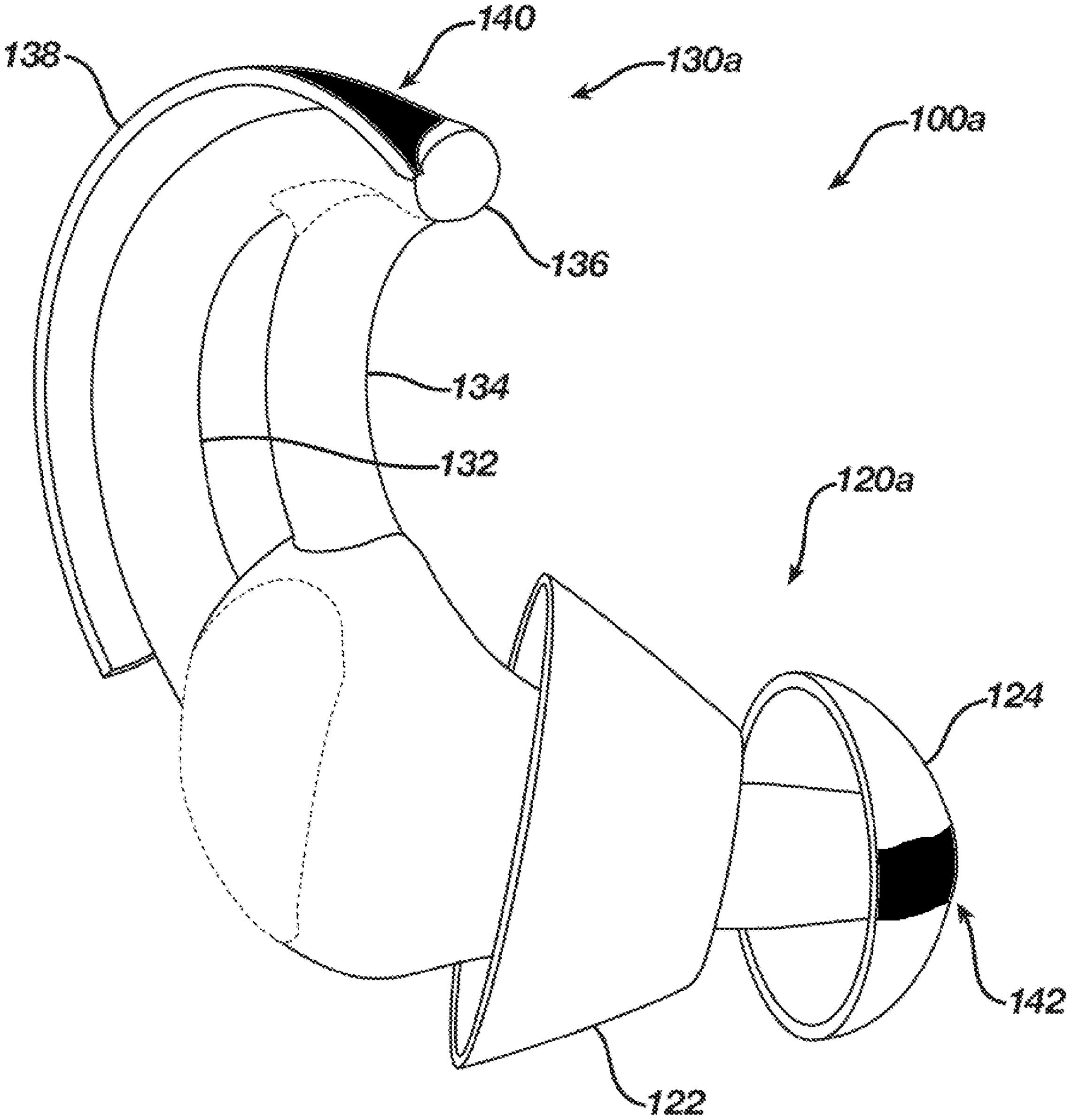
FIG. 2 is another example ear tip.

FIG. 2 illustrates an example ear tip 100*a* similar to the ear tip 100 that includes an extended insertion end 120*a* and an alternate retaining structure 130*a*. Some examples may include the extended insertion end 120*a* without including the alternate retaining structure 130*a*, and some examples may include the alternate retaining structure 130*a* without including the extended insertion end 120*a*.

The alternate retaining structure 130*a* may include an elongated fin 138 formed along a portion of the outer leg 132. The elongated fin 138 is positioned and configured to provide additional surface area contact with the user's skin than the outer leg 132 alone would provide, which may thereby provide additional retention as compared to, e.g., the ear tip 100 of FIG. 1, and provides additional surface area for electrical contact with the user's skin. Each of the retaining structure 130*a* and the elongated fin 138 is configured to rest in the concha of a user's ear when in use, and an upper surface of the elongated fin 138 is in contact with the cymba concha and exerts a small amount of force against the user's cymba concha to enhance retention, and to enhance electrical contact in examples wherein the elongated fin 138 includes one or more electrically conductive elements 140 forming electrodes in contact with the user's cymba concha. Further, the elongated fin 138 may have some flexibility that enhances the ability of the retaining structure 130*a* to fit into the cymba concha, and across a larger portion of the population. The flexibility of the elongated fin 138 also enhances the ability of the electrically conductive elements 140 to maintain good contact with the user's cymba concha.

The extended insertion end 120*a* includes an extension of the insertion end 120 described above to reach into the user's ear canal and includes a mushroom cap 124 configured to form an acoustic seal within the user's ear canal. The tubing connecting the mushroom cap and the umbrella could be solid or hollow. This may enable adjusting insertion path stiffness and affect comfort and stability of the ear tip. In some examples, the extended insertion end 120*a* includes an acoustic channel from the body 120 which, when inserted, may provide acoustic energy from a transducer into the user's ear canal. Reaching further into the user's ear canal than the ear tip 100, and further than conventional ear tips, may provide enhanced performance. The extended insertion end 120 may provide an acoustic channel reaching further into the ear canal, and thereby having an acoustic outlet nearer to the user's ear drum, which may improve performance of active noise reduction (ANR) systems, provide improved acoustic response, and more efficiency (e.g., less acoustic power needed) than conventional ear tips. Additionally, the mushroom cap 124 provides a structure in contact with portions of the user's ear canal and may include one or more electrically conductive elements 142 forming electrodes in contact with the user's ear canal. The extended insertion end 120*a* is configured to place the mushroom cap 124 between an entrance to the ear canal and a first bend in the ear canal. Accordingly, the electrically conductive elements 142 may provide electrical contact with the user's ear canal somewhere between the entrance to the ear canal and the first bend in the ear canal. In various examples, the mushroom cap 124 may include two or more electrically conductive elements 142, such as on either side of the mushroom cap 124 and as more readily illustrated in FIG. 3.

Figure 3:
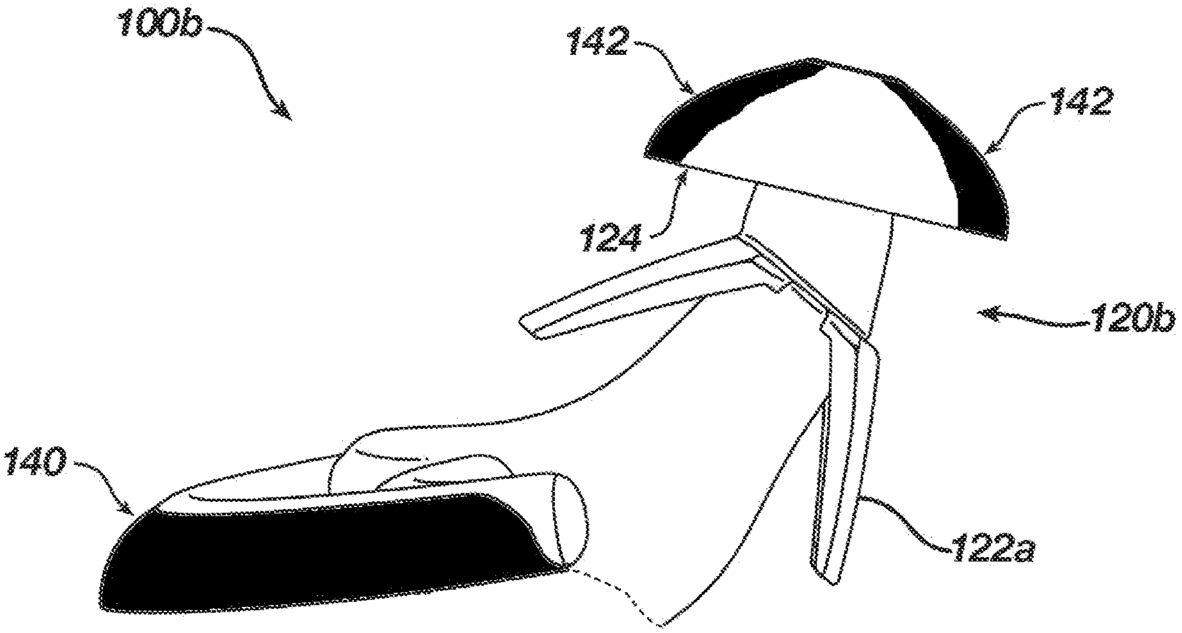
FIG. 3 is another example ear tip.

FIG. 3 illustrates a further example ear tip 100*b* similar to the ear tip 100*a* that includes an alternate extended insertion end 120*b*. The example shown in FIG. 3 includes the alternate retaining structure 130*a*, but in other examples a different or no retaining structure may be provided. The alternate extended insertion end 120*b* includes a bifurcated or split umbrella 122*a*, having two umbrella segments. The split umbrella 122*a* may provide for more easy insertion into the user's ear, as compared to the full umbrella 122. For example, because the extended insertion end 120*b* reaches further into the ear canal (e.g., as compared to the ear tip 100 of FIG. 1), a full umbrella 122 (as in FIG. 2) when in contact with the entrance to the user's ear canal may create forces that cause the mushroom cap 124 to be limited in motion and/or restricted from forming a proper seat within the user's ear canal. According, the split umbrella 122*a* may provide more flexibility for the mushroom cap 124 to properly seat in the user's ear canal and thereby form an acceptable acoustic seal. While the example shown in FIG. 3 includes a split umbrella 122*a* bifurcated into two segments, in other examples the split umbrella 122*a* may be formed of three or more segments. In various examples, the umbrella 122 and/or each of one or more segments of a split umbrella 122*a* may include one or more electrically conductive elements forming electrodes in contact with the user's ear near the entrance to the ear canal.

As described above, in various examples, one or more electrically conductive elements 140, 142 may be provided to form electrodes in contact with portions of the user's ear, in association with the elongated fin 138, the umbrella 122, sections of a split umbrella 122*a*, and/or the mushroom cap 124.

Examples of electrically conductive elements include a metal pad, metal button, metal foils (e.g., gold, silver), metal-salt hybrids (e.g., silver/silver-chloride), polymeric composites (e.g., rubbers compounded with conductive fillers such as carbon black, carbon nanotubes, graphene, silver, glass-coated silver), intrinsically conductive polymers (e.g., poly(3,4-ethylenedioxythiophene) polystyrene sulfonate or PEDOT:PSS), and/or conductive fabric (e.g., fabrics with conductive yarns, fabrics coated with conductive materials). Preferably, the electrically conductive elements are made of soft, flexible materials. The electrically conductive elements can be incorporated on to the ear tip using an ink and applying it using screen printing, pad printing, or in-mold decorating. Alternatively, the conductive elements can be incorporated wholly on to the ear tip via injection, transfer or compression molding. Additional details of example structures and methods of providing electrically conductive elements to form electrodes are included in U.S. patent application Ser. No. 16/448,849, titled EAR TIPS CAPABLE OF CAPTURING BIOELECTRICAL SIGNALS AND PROVIDING NERVE STIMULATION, filed on Jun. 21, 2019, the contents of which are incorporated herein by reference for all purposes.

Electrically conductive elements 140, 142 can function as physiological electrodes for detecting bioelectrical signals of an individual, including, for example, electroencephalogram (EEG), electrooculogram (EOG), electrocardiography (ECG), and electromyogram (EMG) signals, and may also be used to detect pulse rate, respiration rate, body temperature, sweat levels, and glucose, among other health parameters. Monitoring of EEG in a wearable in-ear earpiece can be used, for example, for sleep staging, stress detection, and/or music-to-mood correlation. Monitoring of EOG in a wearable in-ear earpiece can be used, for example, for sensing movement of an individual's eyes. Electrically conductive elements can also be used to deliver an electrical signal to the ear, for example, for use in nerve stimulation.

The ear tip 100 may include an embedded integrated circuit, for example, inside the body 110. In examples, the ear tip 100 is communicably coupled with an integrated circuit that is separate and remotely located, for example, in a computer or a mobile device. The integrated circuit can include a data processor, a memory, and a communication processor. Commands to be executed by the processor can be obtained via the communication processor. The communication processor facilitates wired or wireless communication for the ear tip 100 and can be facilitated via one or more antennas, for example. The communication processor can facilitate communication with one or more networks or other devices, for example, by using wireless methods that are known, including but not limited to Wi-Fi, Bluetooth, 3G, 4G, LTE, and/or ZigBee, among others. The ear tip 100 can further include an embedded power source (e.g., a battery) required to carry out various functionalities involving the integrated circuit and the one or more electronic components described herein.

Various portions of the ear tips, such as those examples illustrated in FIGS. 1-3 and others described can be made of any suitable soft, flexible materials, including, for example, silicone, polyurethane, polynorbornene (e.g., Norsorex® material available from D-NOV GmbH of Vienna, Austria), thermoplastic elastomer (TPE), and/or fluoroelastomer, or others.

Examples of the methods and apparatuses discussed herein are not limited in application to the details of construction and the arrangement of components set forth in the description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, functions, components, elements, and features discussed in connection with any one or more examples are not intended to be excluded from a similar role in any other examples.

Also, the phraseology and terminology used herein is for the purpose of description and should not be regarded as limiting. Any references to examples, components, elements, acts, or functions of the systems and methods herein referred to in the singular may also embrace embodiments including a plurality, and any references in plural to any example, component, element, act, or function herein may also embrace examples including only a singularity. Accordingly, references in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

Having described above several aspects of at least one example, it is to be appreciated various alterations, modifications, and improvements will readily occur to those skilled in the art. Such alterations, modifications, and improvements are intended to be part of this disclosure and are intended to be within the scope of the invention. Accordingly, the foregoing description and drawings are by way of example only, and the scope of the invention should be determined from proper construction of the appended claims, and their equivalents.

What is claimed is:

1. An ear tip for an earpiece, comprising:
a body;
an insertion end coupled to the body and configured to be at least partially inserted into a human ear canal;
a mushroom cap coupled to a distal end of the insertion end and configured to form an acoustic seal in the human ear canal;
a retention structure including an inner leg and an outer leg, each of the inner leg and the outer leg being coupled to the body at a first end and joined together to form a tip at a second end, the outer leg configured to conform, at least in part, to a cymba concha portion of an ear;
an elongated fin projecting laterally from the outer leg and running along at least a portion of a length of the outer leg, the elongated fin being configured to seat against the cymba concha to provide additional contact area than the outer leg alone;
one or more electrically conductive contacts disposed on the elongated fin and configured to provide electrical contact with the cymba concha at the additional contact area; and
one or more electrically conductive elements associated with the mushroom cap and configured to provide electrical contact in the ear canal, between an entrance to the ear canal and a first bend in the ear canal.

2. The ear tip of claim 1 further comprising an umbrella associated with the insertion end, disposed between the body and the mushroom cap and configured to make contact near an entrance to the ear canal.

3. The ear tip of claim 2 further comprising one or more electrically conductive contacts associated with the umbrella to provide one or more electrodes in contact with the ear near the entrance to the ear canal.

4. The ear tip of claim 2 wherein the umbrella is divided into multiple discontinuous segments.

5. The ear tip of claim 2 wherein the umbrella is bifurcated into two opposing segments.

6. An ear tip for an earpiece, comprising:
a body;
an insertion end coupled to the body and configured to be at least partially inserted into a human ear canal;
a retention structure coupled to the body and including an inner leg and an outer leg, the inner leg and the outer leg joined together to form a tip distal from the body, the outer leg configured to conform, at least in part, to a cymba concha portion of an ear; and
an elongated fin projecting laterally from the outer leg and running along at least a portion of a length of the outer leg, the elongated fin being configured to seat against the cymba concha to provide a contact area that is anatomically localized and distinct from the outer leg alone and an electrically conductive contact disposed on the elongated fin to provide an electrode in contact with the cymba concha.

7. The ear tip of claim 6 further comprising an umbrella associated with the insertion end and configured to form an acoustic seal near an entrance to the ear canal.

8. The ear tip of claim 7 further comprising one or more electrically conductive contacts associated with the umbrella to provide one or more electrodes in contact with the ear near an entrance to the ear canal.

9. The ear tip of claim 6 further comprising a mushroom cap coupled to a distal end of the insertion end, the mushroom cap having one or more electrically conductive elements configured to provide electrical contact in the ear canal between an entrance to the ear canal and a first bend in the ear canal.

10. The ear tip of claim 9 further comprising an umbrella associated with the insertion end, disposed between the body and the mushroom cap and configured to make contact with the ear near the entrance to the ear canal.

11. An ear tip for an earpiece, comprising:

a body;

an insertion end coupled to the body and configured to be at least partially inserted into a human ear canal;

a retention structure coupled to the body and including an inner leg and an outer leg, the inner leg and the outer leg joined together to form a tip distal from the body, the outer leg configured to conform, at least in part, to a cymba concha portion of an ear; and an electrically conductive contact disposed on the outer leg to provide an electrode in contact with the cymba concha;

wherein the outer leg further comprises an elongated fin projecting laterally from the outer leg and extending along at least a portion of the outer leg, the electrically conductive contact being disposed on the elongated fin to provide localized electrical contact with the cymba concha distinct from contact provided by the outer leg.

12. The ear tip of claim 11 further comprising an umbrella associated with the insertion end and configured to form an acoustic seal near an entrance to the ear canal.

13. The ear tip of claim 12 further comprising one or more electrically conductive contacts associated with the umbrella to provide one or more electrodes in contact with the ear near the entrance to the ear canal.

14. The ear tip of claim 11 further comprising a mushroom cap coupled to a distal end of the insertion end, the mushroom cap having one or more electrically conductive elements configured to provide electrical contact in the ear canal between the entrance to the ear canal and a first bend in the ear canal.

15. The ear tip of claim 14 further comprising an umbrella associated with the insertion end, disposed between the body and the mushroom cap and configured to make contact with the ear near the entrance to the ear canal.

* * * * *